(12) United States Patent
Johnson et al.

(10) Patent No.: US 6,335,341 B1
(45) Date of Patent: Jan. 1, 2002

(54) PYRIDYL-AND PYRIMIDYL-HETEROCYCLIC COMPOUNDS INHIBITING OXIDO SQUALENE-CYCLASE

(75) Inventors: Michael Clyde Johnson; Nicholas John Newcombe, both of Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/463,326

(22) PCT Filed: Jul. 23, 1998

(86) PCT No.: PCT/GB98/02196

§ 371 Date: Jan. 24, 2000

§ 102(e) Date: Jan. 24, 2000

(87) PCT Pub. No.: WO99/06395

PCT Pub. Date: Feb. 11, 1999

(30) Foreign Application Priority Data

Jul. 29, 1997 (GB) .............................. 9715892

(51) Int. Cl.⁷ .................... C07D 401/06; A61K 31/495; A61K 31/505
(52) U.S. Cl. .................. 514/252.18; 544/295; 546/187; 514/316
(58) Field of Search ..................... 544/295; 514/252.18, 514/316; 546/187

(56) References Cited

FOREIGN PATENT DOCUMENTS

| WO | 96/10022 A | 4/1996 |
| WO | 97/06802 A | 2/1997 |
| WO | 97/28128 A | 8/1997 |
| WO | 98/06705 A | 2/1998 |
| WO | 98/35956 A | 8/1998 |
| WO | 98/35959 A | 8/1998 |

*Primary Examiner*—Mukund J. Shah
*Assistant Examiner*—Hong Liu
(74) *Attorney, Agent, or Firm*—Pillsbury Winthrop LLP

(57) ABSTRACT

This invention concerns heterocyclic derivatives which are useful in inhibiting oxido-squalene cyclase, processes for their preparation and pharmaceutical compositions containing them. The present invention is also concerned with heterocyclic derivatives capable of inhibiting cholesterol biosynthesis and hence in lowering cholesterol levels in blood plasma. The present invention also relates to methods of using such heterocyclic derivatives in treating or preventing diseases and medical conditions such as hypercholesterolemia, atherosclerosis and other medical conditions associated with elevated cholesterol levels. In formula (I):

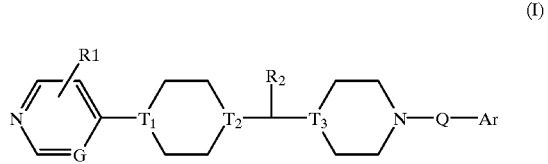

G is selected from CH or N; R1 is selected from hydrogen, halogeno, (1–6C)alkyl, halogeno(1–6C)alkyl, cyano, nitro, (1–6C)alkoxycarbonyl, and $NR^3R^4$ wherein $R^3$ and $R^4$ are independently selected from hydrogen and (1–6C)alkyl, and wherein up to 3 R1 groups may be present; $T_1$ is selected from CH or N; $T_2$ and $T_2$ are independently selected from N and CR, wherein R is selected from hydrogen, hydroxyl and (C1–4)alkyl and wherein either ring containing $T_2$ or $T_3$ is optionally substituted with an oxo group; R2 is selected from hydrogen or (1–4C)alkyl; Q is selected from $SO_2$, CO and $CH_2$; AR is selected from a five or six-membered heterocycle containing up to 3 heteroatoms selected from nitrogen, oxygen and sulphur, phenyl, phenyl (2–6)alkenyl and naphthyl in which any Ar group is optionally substituted by one or more substituents selected from (1–6C)alkyl, halogeno, halogeno (1–6C) alkyl, (1–6C)alkoxy, (1–6C)alkoxycarbonyl, cyano, (1–6C)alkylamido, nitro, $NR^3R^4$ wherein $R^3$ and $R^4$ are independently selected from hydrogen and (1–4C) alkyl; provided that both $T_2$ and $T_3$ are not N and that when $T_2$ is CR then T1 is not CH.

9 Claims, No Drawings

US 6,335,341 B1

PYRIDYL-AND PYRIMIDYL-HETEROCYCLIC COMPOUNDS INHIBITING OXIDO SQUALENE-CYCLASE

This invention concerns heterocyclic derivatives which are useful in inhibiting oxido-squalene cyclase, processes for their preparation and pharmaceutical compositions containing them. The present invention is also concerned with heterocyclic derivatives capable of inhibiting cholesterol biosynthesis and hence in lowering cholesterol levels in blood plasma. The present invention also relates to methods of using such heterocyclic derivatives in treating or preventing diseases and medical conditions such as hypercholesterolemia, atherosclerosis and other medical conditions associated with elevated cholesterol levels.

There is evidence that high serum cholesterol levels are an important risk factor in coronary heart disease and associated diseases such as atherosclerosis and ischaemic heart disease. As a result there has been a great deal of interest in finding ways of lowering cholesterol levels in blood plasma. Although it is possible to obtain some reduction by means of diet, only modest reductions are obtained by controlling the dietary intake of cholesterol. Consequently, there is a need for therapeutic approaches to reducing cholesterol levels.

Several different classes of compounds have been reported which are able to lower cholesterol levels in blood plasma. For example agents which inhibit the enzyme HMGCoA reductase, an enzyme essential for the production of cholesterol, have been reported to reduce levels of serum cholesterol. Illustrative of this class of compounds is the HMGCoA reductase inhibitor known as lovastatin which is disclosed in U.S. Pat. No. 4,231,938. Other agents which are reported to lower serum cholesterol include those which act by complexing with bile acids in the intestinal system and which are hence termed "bile acid sequestrants". It is believed that these agents lower cholesterol levels indirectly by sequestering bile acids within the intestinal tract resulting in lower levels of bile acid circulating in the enteroheptatic system. Replacement of bile acids, which is synthesised in the liver from cholesterol, is promoted. This in turn results in an upregultion of the hepatic LDL cholesterol receptor and in a lowering of circulating blood cholesterol levels.

The biosynthesis of cholesterol is a complex process which will be considered here as three principal stages, namely 1) the conversion of acetic acid to mevalonic acid 2) the conversion of mevalonic acid to squalene and 3) the conversion of squalene to cholesterol. In the last stage, squalene is first converted into 2,3-oxido-squalene and then to lanosterol. Lanosterol is then converted to cholesterol through a number of enzymatic steps.

The conversion of 2,3-oxido-squalene to lanosterol is a key step in the biosynthesis of cholesterol. This conversion is catalysed by the enzyme oxido-squalene cyclase. It follows that inhibition of this enzyme decreases the amount of lanosterol available for conversion to cholesterol. Consequently, inhibition of oxido-squalene cyclase should interupt cholesterol biosynthesis and give rise to a lowering of cholesterol levels in blood plasma.

The present invention is based on the discovery that certain heterocyclic derivatives are inhibitors of oxido-squalene cyclase and are hence useful in treating diseases and medical conditions in which inhibition of oxido-squalene cyclase is desirable.

According to the present invention there is provided a compound of formula I (set out on a seperate sheet following the examples together with the other formulae referred to herein), or a pharmaceutically acceptable salt thereof, wherein:

G is selected from CH or N;

R1 is selected from hydrogen, halogeno, (1–6C)alkyl, halogeno(1–6C)alkyl, cyano, nitro, (1–6C)alkoxycarbonyl, and $NR^3R^4$ wherein $R^3$ and $R^4$ are independently selected from hydrogen and (1–6C)alkyl, and wherein upto 3 R1 groups may be present:

$T_1$ is selected from CH or N;

$T_2$ and $T_3$ are independently selected from N and CR, wherein R is selected from hydrogen, hydroxyl and (C1–4)alkyl and wherein either ring containing $T_2$ or $T_3$ is optionally substituted with an oxo group;

R2 is selected from hydrogen or (1–4C)alkyl;

Q is selected from $SO_2$, CO and $CH_2$;

Ar is selected from a five or six membered heterocycle containing up to 3 heteroatoms selected from nitrogen, oxygen and sulphur, phenyl, phenyl (2–6C)alkenyl and naphthyl in which any Ar group is optionally substituted by one or more substituents selected from (1–6C)alkyl, halogeno, halogeno (1–6C)alkyl, (1–6C)alkoxy, (1–6C)alkoxycarbonyl, cyano, (1–6C)alkylamido, nitro, $NR^3R^4$ wherein $R^3$ and $R^4$ are independently selected from hydrogen and (1–4C)alkyl; provided that both $T_2$ and $T_3$ are not N and that when $T_2$ is CR then $T_1$ is not CH.

The compounds of the present invention are oxido-squalene cyclase inhibitors and hence possess the property of inhibiting cholesterol biosynthesis. Provided as a further feature of the invention is compounds of formula (I), or a pharmaceutically acceptable salt, for use in medical therapy. There is also provided the use of a compound of formula I, or a pharmaceutically acceptable salt thereof, for the manufacture of a medicament for treating diseases or medical conditions in which inhibition of oxidosqualene cyclase is desirable. There is also provided the use of a compound of formula I, or a pharmaceutically acceptable salt thereof, for the manufacture of a medicament for inhibiting cholesterol biosynthesis.

Thus according to a further feature of the present invention there is provided a method of inhibiting oxido-squalene cyclase in a warm-blooded animal (such as man) requiring such treatment, which method comprises adminstering to said animal an effective amount of a compound of formula I, or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

The compounds of the present invention are useful in treating diseases or medical conditions in which inhibition of oxido-squalene cyclase is desirable, for example those in which a lowering of the level of cholesterol in blood plasma is desirable. In particular, the compounds of the present invention are useful in treating hypercholesterolemia and/or ischaemic diseases associated with atheromatous vascular degeneration such as atherosclerosis.

Thus the present invention also provides the use of a compound of formula I, or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

In particular, the compounds of the present invention are potentially useful in inhibiting cholesterol biosynthesis in man and hence in treating the above-mentioned medical conditions in man.

It will be understood that when compounds of formula I contain a chiral centre, the compounds of the invention may exist in, and be isolated in, optically active or racemic form. The invention includes any optically active or racemic form of a compound of formula I which possesses the beneficial pharmacological effect of inhibiting oxido-squalene cyclase. The synthesis of optically active forms may be carried out by standard techniques of organic chemistry well known in the art, for example by, resolution of a racemic form, by synthesis from optically active starting materials or by asymmetric synthesis. It will be appreciated that certain compounds of formula I may exist as geometrical isomers. The invention includes any geometrical isomer of a compound of formula I which possesses the beneficial pharmacological effect of inhibiting oxido-squalene cyclase.

It will also be understood that certain compounds of the present invention may exist in solvated, for example hydrated, as well as unsolvated forms. It is to be understood that the present invention encompasses all such solvated forms which possess the property of inhibiting oxido-squalene cyclase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

Particularly preferred compounds of formula are those wherein:
(i) Q is $SO_2$ or CO, preferably $SO_2$;
(ii) Ar is phenyl, naphthyl, thiophenyl, styryl or pyridyl, preferably phenyl or naphthyl, preferably phenyl;
(iii) R1 is hydrogen or (1–6C)alkyl;
(iv) R2 is hydrogen;
(v) substituents on the heterocyclic rings containing $T^2$ and $T^3$ are (1–6C)alkyl or (2–6C)alkenyl, preferably (1–6C) alkyl, preferably rings containing $T^2$ and $T^3$ are unsubstituted;
(vi) when Ar is substituted by halogeno, halogeno(1–6C) alkyl, (1–6C)alkoxy;
(vii) Ar is unsubstituted phenyl;

Particular values for Ar when a 5- or 6-membered heteroaryl moiety is present are furyl, thienyl, pyrrolyl, pyridyl and, preferably thienyl or pyridyl.

More particularly preferred embodiments are defined below, where substituents are not described they are as defined above.
(i) $T^1$=N, $T^3$=N and Ar is optionally substituted phenyl;
(ii) $T^1$=N, $T^2$=N and Ar is optionally substituted phenyl;
(iii) $T^1$=CH, $T^3$=N and Ar is optionally substituted phenyl;
(iv) $T^1$=CH, $T^2$=N and Ar is optionally substituted phenyl;

Compounds of particular interest include those described in the accompanying examples and their pharmaceutically acceptable salts.

The compounds of formula I and their pharmaceutically acceptable salts may be prepared by processes known to be applicable to the preparation of structurally related compounds. These procedures are illustrated by the following representative processes in which the various groups and radicals such as R1, R2, G, $T_1$, $T_2$, $T_3$, Q and Ar are as defined above (unless stated otherwise), and are provided as a further feature of the present invention. In cases where the compounds contain a group such as an amino, hydroxy, or carboxy group, this group may be protected using a conventional protecting group which may be removed when desired by conventional means. The compounds of formula 1 may be prepared in accordance with the following alternative procedures:

(a) reacting an amine of formula IIA or IIB with a compound of formula III, wherein L is a leaving group or atom (for example chloro or bromo) in the presence of a base, for example triethylamine or pyridine. The reaction is preferably carried out in a suitable inert solvent such as methylene dichloride, tetrahydrofuran or water and at a temperature range of from −20 to 50° C., conveniently at or near ambient temperature;

(b) reducing a compound of formula IV. Suitable agents to effect the reduction of compounds of formula IV include borane complexes, such as borane-dimethylsulphide, and complex metal hydrides, such as aluminium lithium hydride. The reaction is preferably carried out in a suitable inert solvent, such as tetrahydrofuran or diethylether, and at a temperature range of from 0 to 25° C.;

(c) reacting a compound of formula V, where $T_1$ is N, with a compound of formula VI, in which Z is a displaceable group, such as halo (for example chloro). The reaction is preferably carried out in the presence of a base, such as sodium hydrogencarbonate, triethylaamine or pyridine and in a suitable inert solvent, such as an alcohol (for example ethanol), methylene chloride or tetrahydrofuran, at a temperature range of from 20 to 120° C.;

Compounds of formula IIA may be prepared by reductive amination, reacting a compound of formula VII, where $T^2$ is N and X is H, with a compound of formula VIII, where $T^3$ is CH, Y is CHO or COR2 and P is a protecting group (for example benzyloxycarbonyl), and subsequently effecting removal of the protecting group. Alternatively compounds of formula IIA may be prepared by reductive amination, reacting a compound of formula VII, where $T^2$ is CH and X is CHO or COR2, with a compound of formula VIII, where $T^3$ is N, Y is H and P is a protecting group (for example benzyloxycarbonyl), and subsequently effecting removal of the protecting group. Each reductive amination reaction is preferably carried out in a suitable inert solvent, such as an alcohol (for example methanol), and at a temperature range of 0° C. to ambient temperature, and in the presence of a suitable reducing agent, such as a borane complex, for example sodiumcyanoborane hydride.

Alternatively compounds of formula IIA may be prepared by reacting a compound of formula X, wherein P is a protecting group (for example benzyloxycarbonyl), with a compound of formula VI in an analogous manner as described in method c) above.

Compounds of formula IIB may be prepared by reacting a compound of formula IX with a compound of formula VIII, wherein $T^3$ is N, Y is H and $P^1$ is a protecting group, and subsequently effecting removal of the protecting group. Preferable the reaction is carried out in a suitable inert solvent such as aqueous alcohol (for example aqueous propanol) at a temperature range of from 60–140° C. Removal of the protecting group is by reaction corresponding to the particular protecting group used (for example for benzyloxycarbonyl by hydrogenation in the presence of a catalyst such as palladium-on-carbon).

Compounds of formula IV may be prepared in accordance with the procedures described in WO 97/06802.

Compounds of formula VII, where X is CHO, and compounds of formula VIII, where Y is CHO, may be prepared by reduction of the corresponding Weinreb amide, suitably using a complex metal hydride such as lithium aluminium hydride.

Compounds of formula IX may be prepared by reacting a compound of formula VII, where $T_2$ and X form a carbonyl group, to form the epoxide. Epoxide formation is effected by trimethyl sulpoxonium iodide (coreyylide).

A suitable protecting group for an amino or alkylamino group is, for example, an acyl group for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an oreganic acid such as trifluoroacetic acid, or for example a benzyl group which may be removed, for example, by hydrogenation over a catalyst such as palladium-on-carbon.

As mentioned above, it will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. The protecting groups may be removed at any convenient stage in the synthesis using conventional techniques well known in the chemical art.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Fiedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

When an optically active form of a compound of the formula I is required, it may be obtained, for example, by carrying out one of the aforesaid procedures using an optically active starting material or by resolution of a racemic form of said compound using a conventional procedure.

As mentioned previously, the compounds of the formula I (and their pharmaceutically-acceptable salts) are inhibitors of the enzyme oxido-squalene cyclase. Thus, the compounds of the present invention are capable or inhibiting cholesterol biosynthesis and hence in lowering choleserol levels in blood plasma.

The beneficial pharmacological properties of the compounds of the present invention may be demonstrated using one or more of the following techniques.

(a) In vitro Test to Measure Inhibition of Oxido-squalene Cyclase

This test measures the inhibition of microsomal oxido-squalene cyclase in vitro by compounds at set concentrations in the incubation medium.

Microsomes are prepared from rat liver according to methods known in the art, for example, the method described in published European Patent Application No 324,421 and stored in liquid nitrogen prior to assay. Assay vials are kept at 37° C. throughout the incubation. The microsomes typically contain 15–20 mg of protein per ml of microsomes. For 7.4.

Phosphate buffered Tween 80 (polyoxyethylene sorbitan monolaurate) is prepared by adding 0.1 g tween 80 to 100 ml of 50 mM phosphate buffer.

A stock solution of oxido-squalene is made up as a solution in ethanol (0.65 mg. ml.$^{-1}$). 18 $\mu$l of radio-labelled oxido-squalene (1 $\mu$Ci.ml$^{-1}$) is evaporated to dryness under a stream of nitrogen and redissolved in 1 ml of ethanol and 1 ml of the stock solution of oxido-squalene is added.

The test compound is dissolved in dimethyl sulphoxide to give a 10$^{-4}$M stock solution. Dilutions are made from the stock to give 10$^{-5}$M, 10$^{-6}$M etc.

Phosphate buffered Tween 80 (28 $\mu$l) is placed in 5 ml disposable plastic vials and 4 $\mu$l of the solution of the test compound is added and mixed well. An aliquot of the oxido-squalene mix (15 $\mu$l) is added and the vials pre-incubated for 10 minutes at 37° C. A portion of the microsomes (14.6 $\mu$l) are then added and incubated for a further 1 hour. The reaction is stopped by the addition of 315 $\mu$l of a mixture of 16% KOH in 20% ethanol.

The samples are then placed in a water bath at 80° C. for 2 hours to saponify. At the end of this process water (630 μl) is added followed by hexane (5 ml). The samples are tumble mixed for 5 minutes and then centrifuged. The hexane phase is removed and evaporated under nitrogen. The samples are then reconstituted in 300 μl of a 80:20 mixture of a acetonitrile:isopropyl alcohol. The samples are then chromatographed using a Hichrom 30DsS1 column with an isocratic elution using a 95:5 mixture of acetonitrile:isopropyl alcohol and a flow rate of 1 ml.min$^{-1}$. The output from the UV detector is connected to a radio-chemical detector to visualise radiolabelled sterols. Reaction rate is measured as the conversion of oxido-squalene to lanosterol, and the effects of test compounds are expressed as an inhibition of this process.

(b) In vivo Test to Measure Inhibition of Oxido-squalene Cyclase

The ability of a compound to inhibit oxido-squalene cyclase and/or inhibit cholesterol biosynthesis may be assessed by a routine laboratory procedure carried out in the rat. The test involves administration of the compound to rats on a reversed lighting regimen. Female rats (35–55 g) are housed in reverse lighting conditions (red light from 0200 h–1400 h) for a period of about 2 weeks prior to test. Animals are allowed free access to chow and drinking water throughout this period. At test, animals should weigh 100–140 g. The rats are dosed orally with the compound (typically 10–50 mg/kg) formulated in apolyethylene glycol/hydroxypropylmethyl cellulose mix. After 1 hour the rats are given triturated sodium mevalonate (15 μCi/kg) intraperitoneally. Two hours after administration of the compound the rats are terminated and a piece of liver removed and weighed. The tissue is saponified at 80° C. for 2 hours in an ethanolic/potassium hydroxide solution (80% w/v aqueous KOH diluted 1:10 with ethanol). Water (2 ml) is added and the mixture extracted wiht iso-hexane (2×5 ml). The organic extracts are combined, evaporated to dryness under a stream of nitrogen and the residue is dissolved in a mixture of acetonitrile/iso-propanol (300 μl). An aliquot (200 μl) of this solution is loaded onto a HPLC column to separate the sterols. The radio-label content of each fraction is assessed using a radio chemical flow detector. Inhibitors of oxido squalene cyclase are classed as those compounds which caused a build up of substrate and a concomitant disappearance of cholesterol and its precursors. $ED_{50}$ values are generated in the usual manner.

As mentioned previously, the compounds of the present invention are inhibitors of oxido-squalene cvclase and hence possess the property of inhibiting cholesterol biosynthesis. Thus the compounds of the present invention will be useful in treating diseases or medical conditions in which an inhibition of choleserol biosynthesis or lowering of cholesterol levels in blood plasma is desirable, for example, hypercholesterolemia and/or ischaemic diseases associated with atheromatous vascular degeneration such as atherosclerosis.

When used in the treatment of diseases and medical conditions such as those mentioned above it is envisaged that a compound of formula I, or a pharmaceutically acceptable salt thereof, will be administered orally intravenously, or by some other medically acceptable route so that a dose in the general range of, for example, 0.01 to 10 mg per kg body weight is received. However it will be understood that the precise dose administered will necessarily vary according to the nature and severity of the disease, the age and sex of the patient being treated and the route of administration.

In general, the compounds of formula I, or a pharmaceutically-acceptable salt thereof, will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I, or a phannaceutically-acceptable salt thereof, in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease.

As inhibitors of oxido-squalene cyclase, the compounds of the present invention may also find utility as antifungal agents, and so the present invention also provides a method of inhibiting cholesterol biosynthesis in fungi. In particular the present invention provides a method of treating fungal infections which comprises administration to a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

The invention will now be illustrated by the following non-limiting Examples in which, unless otherwise stated:

(i) evaporations were carried out by rotary evaporation in vacuo;

(ii) operations were carried out at room temperature, that is in the range 18–26° C.;

(iii) flash column chromatography or medium pressure liquid chromatography (MPLC) was performed on silica gel (Merck Kieselgel Art.9385, obtained from E Merck, Darmstadt, Germany);

(iv) yields are given for illustration only and are not necessarily the maximum attainable by diligent process development;

(v) proton NMR spectra were normally determined at 200 MHz using tetramethylsilane (TMS) as an internal standard, and are expressed as chemical shifts (delta values) obtained in DMSO-$d_6$ (unless stated otherwise) in parts per million relative to TMS using conventional abbreviations for designation of major peaks: s, singlet, m, multiplet; t, triplet; br, broad; d, doublet;

(vi) all end-products were characterised by microanalysis, NMR and/or mass spectroscopy.

EXAMPLE 1

A solution of 4-chlorophenylsulphonyl chloride (1.78 g) in methylene chloride (10 ml) was added dropwise over 15 minutes to a mixture of 4-[1-(2-methylpyrimidin-4-yl) piperazine-4-ylmethyl]piperidine trihydrochloride (2.78 g) and triethylamine (6.72 ml) in dichloromethane (40 ml) at 0° C. The solution was stirred at ambient temperature for 18 hours. The solution was diluted with dichloromethane and washed with water, dried (Na₂SO₄) and evaporated. The residue was purified by chromatography eluting with 4% methanol in dichloromethane. Recrystallisation from ethyl acetate/hexane gave, as a solid 1-(4-chlorophenylsulphonyl)-4-[1-(2-methylpyrimidin-4-yl) piperazin-4ylmethyl]piperidine (2.50 g), mp 191–193° C. (decomp.).

¹HNMR (CDCl₃): 1.30 (m, 2H), 1.40 (m, 1H), 1.80 (m, 2H), 2.20 (d, 2H), 2.3 (dd, 2H), 2.40 (m, 4H), 2.50 (s, 3H), 3.60 (m, 4H), 3.80 (m, 2H), 6.30 (d, 1H), 7.50 (d, 2H), 7.70 (d, 2H) and 8.10 (d, 1H); m/z 450 (M+1).

The starting material was prepared as follows:

To a solution of N-t-butoxycarbonyl isonipecotic acid (7.20 g) and N,O-dimethylhydroxylamine hydrochloride (3.68 g) in dichloromethane (100 ml) was added 1-(3-dimethylaminopropyl)-3-ethylcarbodiimide hydrochloride (7.23 g), N-hydroxybenzotriazole (5.10 g) and triethylamine (10.52 ml) The resulting solution was stirred at ambient temperature for 18 hours. The solution was diluted with dichloromethane and washed with water, 2M aqueous citric acid solution, saturated aqueous sodium bicarbonate solution, dried (Na₂SO₄) and evaporated to give 1-(tert-butoxycarbonyl)-4-(N,O-dimethylhydroxylarnino carbonyl) piperidine (8.01 g) as an oil.

¹HNMR (CDCl₃): 1.40 (s, 9H), 1.70 (m, 4H), 2.80 (m, 3H), 3.20 (s, 3H), 3.70 (s, 3H), 4.20 (m, 2H); m/z273 (M+1).

To a solution of 1-(tert-butoxycarbonyl)-4-(N,O-dimethylhydroxylamino carbonyl)piperidine (8.00 g) in tetrahydrofuran (150 ml) at 0° C. was added lithium aluminium hydride (1.23 g) portionwise over 5 minutes. The resulting suspension was stirred at 0° C. for 3 hours and then water (1 ml), 2M aqueous sodium hydroxide solution (1 ml) and water (4 ml) were added and the suspension filtered through celite. The filter cake was washed with dichloromethane and the combined organic extracts evaporated to give 1-(tert-butoxycarbonyl)-4-(formyl)piperidine (7.04 g) as an oil.

¹HNMR (CDCl₃): 1.40 (s, 9H), 1.60 (m, 2H), 2.40 (m, 1H), 2.90 (m, 2H), 3.40 (d, 1H), 4.00 (m, 3H), 9.70 (s, 1H).

To a solution of 1-(tert-butoxycarbonyl)-4-(formyl) piperidine (7.14 g) and 1-(2-methylpyrimidin-4-yl) piperazine dihydrochloride (8.38 g) in methanol/acetic acid (99:1) (150 ml) was added sodium cyanoborohydride (6.32 g) portionwise over 30 minutes and the resultant suspension stirred at arnbient temperature for 3 hours. The suspension was quenched by addition of saturated aqueous sodium bicarbonate solution and the resulting mixture extracted with ethyl acetate. The organic phase was dried (Na₂SO₄) and evaporated. The residue was purified by chromatography eluting with 5% methanol in dichloromethane to give 1-tert-butoxycarbonyl-4-[1-(2-methylpyrimidin-4-yl)piperazin-4-ylmethyl]piperidine (3.02 g) as a foam.

¹H NMR (CDCl₃): 1.10 (m, 2H), 1.40 (s, 9H), 1.80 (m, 2H), 2.20 (d, 2H), 2.45 (m, 4H), 2.50 (s, 3H), 2.70 (dd, 2H), 3.60 (m, 4H), 4.10 (m, 2H), 6.35 (d, 1H), 8.10 (d, 1H); m/z 377 (M+1).

Ethyl acetate saturated with gaseous HCl (50 ml) was added to a solution of 1-tert-butoxycarbonyl-4-[1-(2-methylpyrimidin-4-yl)piperazin-4-ylmethyl]piperidine (3.02 g) in ethyl acetate (15 ml) and the resulting suspension stirred at ambient temperature for 3 hours. Solvent was evaporated to give 4-[1-(2-methylpyrimidin-4-yl)piperazin-4-ylmethyl]piperidine trihydrochloride (2.78 g) as a colourless foam.

¹HNMR (d6-DMSO): 1.40 (m, 2H), 2.00 (m, 2H), 2.20 (m, 1H), 2.60 (s, 3H), 2.80 (dd, 2H), 3.10 (m, 4H), 3.20 (m, 2H), 3.60–3.80 (m, 6H, partially obscured by HOD peak); m/z 276 (M+1).

EXAMPLE 2

Using an analogous procedure to that described in Example 1, 4-[1-(2-methylpyrimidin-4-yl)piperazin-4-ylmethyl]piperidine trihydrochloride was reacted with the appropriate sulphonyl chloride to give the compounds listed below in table 1

TABLE 1

| No. | R | mp ° C. | ¹H NMR (CDCl₃) |
|---|---|---|---|
| 1 | 4-bromo-phenyl-sulphonyl | 167–171 (decomp.) | 1.30(m, 2H), 1.40(m, 1H), 1.80(m, 2H), 2.20(d, 2H), 2.30(dd, 2H), 2.40(m, 4H), 2.50(s, 3H), 3.60(m, 4H), 3.80(m, 2H), 6.30(d, 1H), 7.60(d, 2H), 7.70(d, 2H), 8.10(d, 1H) |
| 2 | 4-trifluoro-methyl-phenyl-sulphonyl | 154–155 | 1.30(m, 2H), 1.40(m, 1H), 1.80(m, 2H), 2.20(d, 2H), 2.30(dd, 2H), 2.40(m, 4H), 2.50(s, 3H), 3.60(m, 4H), 3.80(m, 2H), 6.30(d, 1H), 7.80(d, 2H), 7.90(d, 2H), 8.10(d, 1H) |
| 3 | phenyl-sulphonyl | 157–158 | 1.30(m, 2H), 1.40(m, 1H), 1.80(m, 2H), 2.20(d, 2H), 2.30(dd, 2H), 2.40(m, 4H), 2.50(s, 3H), 3.60(m, 4H), 3.80(m, 2H), 6.30(d, 1H), 7.60(m, 3H), 7.80(dd, 2H), 8.10(d, 1H) |
| 4 | 4-methoxy-phenyl-sulphonyl | 157–158 | 1.30(m, 2H), 1.40(m, 1H), 1.80(m, 2H), 2.20(d, 2H), 2.30(dd, 2H), 2.40(m, 4H), 2.50(s, 3H), 3.60(m, 4H), 3.80(m, 2H), 3.90(s, 3H), 6.30(d, 1H), 7.00(d, 2H), 7.70(d, 2H), 8.10(d, 1H) |

EXAMPLE 3

A solution of 4-bromophenylsulphonyl chloride (411 mg) in methylene chloride (4 ml) was added dropwise over 15 minutes to a mixture of 4-[4-(4-pyridyl)-1-piperidylmethyl] piperidine trihydrochloride (545 mg) and triethylamine (1.07 ml) in dichloromethane (10 ml) at 0° C. The solution was stirred at ambient temperature for 18 hours. The solution was diluted with dichloromethane and washed with water, dried (Na₂SO₄) and evaporated. The residue was purified by chromatography eluting with 4% methanol in dichloromethane. Recrystallisation from ethyl acetate/ hexane gave, as a solid 1-(4-bromophenylsulphonyl)-4-[4-(4-pyridyl)-1-piperidylmethyl]piperidine (410 mg), mp 163–164° C.

¹HNMR (CDCl₃): 1.30 (m, 2H), 1.40 (m, 1H), 1.80 (m, 6H), 2.00 (dd, 2H), 2.20 (d, 2H), 2.30 (dd, 2H), 2.40 (m, 1H), 2.90 (m, 2H), 3.80 (m, 2H), 7.10 (d, 2H), 7.60 (d, 2H), 7.70 (d, 2H) and 8.50 (d, 2H); m/z 478 (M+1).

The starting material was prepared as follows:

To a solution of 1-(tert-butoxycarbonyl)-4-(formyl) piperidine (2.59 g) and 4-(4-pyridyl)piperidine (1.97 g) in methanol/acetic acid (99:1) was added sodium cyanoborohydride (2.29 g) portionwise over 30 minutes and the resultant suspension stirred at ambient temperature for 3 hours. The suspension was quenched by addition of saturated aqueous sodium bicarbonate solution and the resulting mixture extracted with ethyl acetate. The organic phase was dried (Na$_2$SO$_4$) and evaporated. The residue was purified by chromatography eluting with 5% methanol in dichloromethane to give 1-tert-butoxycarbonyl-4-[4-(4-pyridyl)-1-piperidylmethyl]piperidine (1.65 g) as a solid.

$^1$HNMR (CDCl$_3$): 1.10 (m, 2H), 1.40 (s, 9H), 1.80 (m, 7H), 2.00 (dd, 2H), 2.20 (d, 2H), 2.50 (m, 1H), 2.70 (m, 2H), 3.00 (m, 2H), 4.10 (m, 2H), 7.20 (d, 2H) and 8.50 (d, 2H); m/z 361 (M+1).

Ethyl acetate saturated with gaseous HCl (50 ml) was added to a solution of 1-tert-butoxycarbonyl-4-[4-(4-pyridyl)-1-piperidylmethyl]piperidine (1.65 g) in ethyl acetate (25 ml) and the resulting suspension stirred at ambient temperature for 3 hours. Solvent was evaporated to give 4-[4-(4-pyridyl)-1-piperidylmethyl]piperidine trihydrochloride (1.60 g) as a colourless foam.

$^1$HNMR (d6-DMSO): 1.40 (m, 2H), 2.00 (m, 4H), 2.20 (m, 1H), 2.40 (m, 1H), 2.80 (m, 2H), 3.00 (m, 4H), 3.20 (m, 4H), 3.60 (m, 2H), 7.90 (d, 2H) and 8.80 (d, 2H); m/z 260 (M+1).

EXAMPLE 4

Using an analogous procedure to that described in Example 3,4-[4-(4-pyridyl)-1-piperidylmethyl] piperidinetribydrochloride was reacted with appropriate sulphonyl chloride to give the compounds listed below in table 2.

TABLE 2

| No. | R | mp ° C. | $^1$HNMR (CDCl$_3$) |
|---|---|---|---|
| 1 | 4-trifluoro-methyl-phenyl-sulphonyl | 156–157 | 1.30(m, 2H), 1.40(m, 1H), 1.80(m, 6H), 2.00(dd, 2H), 2.20(d, 2H), 2.30(dd, 2H), 2.40(m, 1H), 2.90(m, 2H), 3.80(m, 2H), 7.10(d, 2H), 7.80(d, 2H), 7.90(d, 2H) and 8.50(d, 2H) |
| 2 | phenyl-sulphonyl | 126–127 | 1.30(m, 2H), 1.40(m, 1H), 1.80(m, 6H), 2.00(dd, 2H), 2.20(d, 2H), 2.30(dd, 2H), 2.40(m, 1H), 2.90(m, 2H), 3.80(m, 2H), 7.10(d, 2H), 7.60(m, 3H), 7.80(d, 2H) and 8.50(d, 2H) |

EXAMPLE 5

1-(4-Bromophenylsulphonyl)-4-[1-(2-methylpyrimidin-4-yl)-piperazin-4-ylcarbonyl]-4-methylpiperidine (261.3 mg) suspended in dry THF (2 ml) was treated with excess borane methyl sulphide complex (0.3 ml) at reflux. After 3 hours the reaction was left open for solvent and excess BH$_3$.Me$_2$S to evaporate. The residue was dissolved in 2 ml THF and stirred 2 hours with 0.1 ml 6M HCl. The reaction mixture was basified with 2N NaOH solution, then partitioned between dichloromethane and water. The dichloromethane solution was washed with brine, dried (MgSO$_4$) and evaporated to give 226 mg of a solid. The residue was chromatographed on a Bondelut (CH$_2$Cl$_2$ then 1% MeOH/CH$_2$Cl$_2$/1% NH$_4$OH) to give 113 mg of 1-(bromophenylsulphonyl)-4-[1-(2-methylpyrimidin-4-yl)-piperazin-4-ylmethyl]-4-methylpiperidine product as a foam.

$^1$H-NMR (CDCl3): 0.82(s, 3H), 1.36(d, 2H), 1.6–1.73(m, 2H), 2.14(s, 2H), 2.5(s, 2H), 2.54(t, 4H), 2.68(t, 2H), 3.4–3.5 (m, 2H), 3.6(br s, 4H), 6.28(d, 1H), 7.6–7.72(m, 4H), 8.12(d, 1H).

EXAMPLE 6

A solution of 4-trifluoromethylphenylsulphonylchloride (367 mg) in methylene chloride (5 ml) was added dropwise over 5 minutes to a mixture of 4-[1-(2-methylpyrimidin-4-yl)-4-piperidylmethyl]piperazine trihydrochloride (625 mg) and triethylamine (1.04 ml) in dichloromethane (20 ml) at 0° C. The solution was stirred at ambient temperature for 18 hours. The solution was diluted with dichloromethane and washed with water, dried (Na$_2$SO$_4$) and evaporated. The residue was purified by chromatography eluting with 1–2% methanol in dichloromethane. Filtration from ether gave 1-(4-trifluoromethylphenylsulphonyl)-4-[1-(2-methylpyrimidin-4-yl)-4-piperidyimethyl]piperazine (358 mg), as a solid, mp 135–136° C.

$^1$HNMR (CDCl$_3$): 1.08 (m, 2H), 1.77 (m, 3H), 2.20 (d, 2H), 2.47 (s, 3H), 2.53 (m, 4H), 2.80 (m, 2H), 3.06 (m, 4H), 4.38 (m, 2H), 6.26 (d, 1H), 7.81 (d, 2H), 7.90 (d, 2H), 8.08 (d, 1H).

The starting material was prepared as follows:

To a solution of 1-(2-methylpyrimidin-4-yl)piperidine-4carboxylic acid (30.81 g) and N,O-dimethylhydroxylamine hydrochloride (11.91 g) in dichloromethane (300 ml) was added 1-(3-dimethylaminopropyl)-3-ethylcarbodiimide hydrochloride (23.41 g), N-hydroxybenzotriazole (16.50 g) and triethylamine (34.00 ml). The resulting solution was stirred at ambient temperature for 18 hours. The solution was diluted with dichloromethane and washed with water. 2M aqueous citric acid solution, saturated aqueous sodium bicarbonate solution, dried (Na$_2$SO$_4$) and evaporated to give 1-(2-methylpyrimidin-4-yl)-4-(N,O-dimethylhydroxylaminocarbonyl)piperidine (25.50 g) as a cream solid.

$^1$HNMR (CDCl$_3$): 1.80 (m, 4H), 2.50 (s, 3H), 3.00 (m, 3H), 3.20 (s, 3H), 3.70 (s, 3H), 4.40 (m, 2H), 6.30 (d, 1H), 8.10 (d, 1H); m/z 265 (M+1).

To a solution of 1-(2-methylpyrimidin-4-yl)-4-(N,O-dimethylhydroxylaminocarbonyl)piperidine (2.89 g) in tetrahydrofuran (50 ml) at 0° C. was added lithium aluminium hydride (457 mg) portionwise over 5 minutes. The resulting suspension was stirred at 0° C. for 3 hours and then water (0.62 ml). 2M aqueous sodium hydroxide solution (0.62 ml) and water (1.86 ml) were added and the suspension filtered through celite. The filter cake was washed with dichloromethane and the combined organic extracts evaporated to give 1-(2-methylpyrimidin-4-yl)-4-(formyl)piperidine (2.40 g) as an oil.

NMR (CDCl$_3$): 1.70 (m, 2H), 2.00 (m, 2H), 2.50 (s, 3H), 2.60 (m, 1H), 3.20 (m, 2H), 4.20 (m, 2H), 6.30 (d, 1H), 8.10 (d, 1H), 9.70 (s, 1H); m/z 206 (M+1), 238 (M+MeOH).

To a solution of 1-(2-methylpyrimidin-4-yl)-4-(formyl) piperidine (4.25 g) and N-t-butoxycarbonyl piperazine (5.34 g) in methanol/acetic acid (99:1) (100 ml) was added sodium cyanoborohydride (5.41 g) portionwise over 30 minutes and the resultant suspension stirred at ambient temperature for 3 hours. The suspension was quenched by addition of saturated aqueous sodium bicarbonate solution and the resulting mixture extracted with ethyl acetate. The organic phase was dried (Na$_2$SO$_4$) and evaporated. The residue was purified by chromatography eluting with 10% methanol in ethylacetate to give 1-(tert-butoxycarbonyl)-4-[1-(2-methylpyrimidin-4-yl)-4-piperidylmethyl]piperazine (2.85 g) as a solid.

NMR (CDCl$_3$): 1.16 (m, 2H), 1.48 (s, 9H), 1.83 (m, 3H), 2.20 (d, 2H),2.32 (m, 4H), 2.50 (s, 3H), 2.83 (m, 2H), 3.40 (m, 4H), 4.40 (m, 2H), 6.30 (d, 2H), 8.18 (d, 2H); m/z 375 (M+1).

Ethyl acetate saturated with gaseous HCl (30 ml) was added to 1-(tert-butoxycarbonyl)-4-[1-(2-methylpyrimidin-4-yl)-4-piperidylmethyl)]piperazine (2.8 g) and the resulting suspension stirred at ambient temperature for 3 hours. Solvent was evaporated to give 4-[1-(2-methylpyrimidin-4-yl)-4-piperidylmethyl]piperazine trihydrochloride (3.11 g) as a white solid.

m/z 276 (M+1).

EXAMPLE 7

Using an analogous procedure to that described in Example 6, 4-[1-(2-methylpyrimidin-4-yl)-4-piperidylmethyl]piperazine trihydrochloride was reacted with appropriate sulphonyl chloride to give the compounds listed below in table 3.

TABLE 3

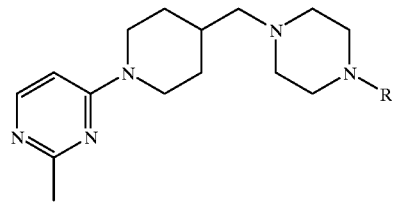

| No. | R | mp ° C. | $^1$H NMR (CDCl$_3$) |
|---|---|---|---|
| 1 | 4-bromo-phenyl-sulphonyl | 167–168 | 1.10(m, 2H), 1.80(m, 3H), 2.20(d, 2H), 2.45(s, 3H), 2.50(m, 4H), 2.80(dd, 2H), 3.00(m, 4H), 4.40(m, 2H), 6.30(d, 1H), 7.60(d, 2H), 7.70(d, 2H), 8.10(d, 1H). |
| 2 | phenyl-sulphonyl | 151–153 | 1.10(m, 2H), 1.80(m, 3H), 2.20(d, 2H), 2.50(m, 7H), 2.80(dd, 2H), 3.06(m, 4H), 4.40(m, 2H), 6.30(d, 1H), 7.60(m, 3H), 7.80(m, 2H), 8.10(d, 1H). |
| 3 | 4-fluoro-phenyl-sulphonyl | 163–165 | 1.10(m, 2H), 1.80(m, 3H), 2.20(d, 2H), 2.50(m, 7H), 2.80(dd, 2H), 3.06(m, 4H), 4.40(m, 2H), 6.30(d, 1H), 7.25(m, 2H), 7.80(m, 2H), 8.10(d, 1H). |
| 4 | 4-methoxy-phenyl-sulphonyl | 164 | 1.10(m, 2H), 1.80(m, 3H), 2.20(d, 2H), 2.45(s, 3H), 2.50(m, 4H), 2.80(dd, 2H), 3.00(m, 4H), 3.90(s, 3H), 4.40(m, 2H), 6.30(d, 1H), 7.00(d, 2H), 7.70(d, 2H), 8.10(d, 1H). |

EXAMPLE 8

A solution of 4-fluorobenzoyl chloride(238 mg) in methylene chloride (5 ml) was added dropwise over 5 minutes to a mixture of 4-[-1-(2-methylpyrimidin-4-yl)-4-piperidylmethyl]piperazine trihydrochloride (625 mg) and triethylamine (1.04 ml) in dichloromethane (20 ml) at 0° C. The solution was stirred at ambient temperature for 18 hours. The solution was diluted with dichloromethane and washed with water, dried (Na$_2$SO$_4$) and evaporated. The residue was purified by chromatography eluting with 1–2% methanol in dichloromethane. Filtration from ether gave 1-(4-fluorobenzoyl)-4-[1-(2-methyl-4-pyrimidinyl)-4-piperidylmethyl]piperazine, as a solid (244 mg), mp 127–128° C.

$^1$H NMR (CDCl$_3$): 1.10 (m, 2H), 1.80 (m, 3H), 2.20 (d, 2H), 2.50 (m, 7H), 2.85 (m, 2H), 3.60 (m, 4H), 4.40 (m, 2H), 6.30 (d, 1H), 7.10 (m, 2H), 7.40 (m, 2H), 8.10 (d, 1H).

The starting material was prepared as for Example 6.

EXAMPLE 9

A solution of 4-trifluoromethylphenylsulphonylchloride (0.44 g) in dichloromethane (3 ml) was added to a mixture of 1-(2-methylpyrimidin-4-yl)-4-(piperazin-1-ylmethyl) piperidin-4-ol hydrochloride (0.53 g) and triethylamine (1.0 ml) in dichloromethane (30 ml) at 5° C. The solution was stirred at ambient temperature for 16 hours. The solution was evaporated to dryness. The residue was dissolved in dichloromethane and the solution was washed with water, dried (Na$_2$SO$_4$) and evaporated to dryness. The residue was purified by flash column chromatography on silica (Bond Elut 10 g), using 0.5–3% methanol in dichloromethane as eluent. Recrystallisation from ethyl acetate/isohexane gave 1-(4-trifluoromethylphenylsulphonyl )-4-[1-(2-methylpyrimidin-4-yl)-4-piperidyl-4-olmethyl]piperazine, as a colourless solid (0.53 g), mp155–156° C.

$^1$HNMR (CDCl$_3$): 1.5 (m, 4H), 2.35 (s, 2H), 2.5 (s, 3H), 2.75 (m, 5H), 3.05 (m, 4H), 3.25 (m, 2H), 4.2 (m, 2H), 6.30 (d, 1H), 7.85 (q, 4H), 8.10 (d, 1H); m/z 500 (M+1).

The starting material was prepared as follows:

A mixture of 2-methyl-4,6-dichloropyrimidine (12.2 g), 4-piperidinone monohydrate monohydrochloride (10.9 g) and triethylamine (42 ml) in ethanol (300 ml) was heated to reflux. The resulting solution was stirred at reflux for 18 hours. The solution was evaporated to dryness. The solid residue was partitioned between ethyl acetate (1 l) and water (50 ml). The ethyl acetate layer was washed with water (3×50 ml), saturated brine (50 ml), dried (Na$_2$SO$_4$) and evaporated to dryness. The solid residue was recrystallised from ethyl acetate/isohexane to give a cream solid. This was further purified by column chromatography on alumina (ICN alumina N32-63), using dichloromethane as eluent, to give 1-(6-chloro-2-methylpyrimidin-4-yl)piperidin-4-one (14.0 g) as an off-white solid.

$^1$HNMR (CDCl$_3$): 2.5 (s, 3H), 2.55 (m, 4H), 3.95 (m, 4H), 6.4 (s, 1H); m/z 226 (M+1).

Powdered trimethyl sulphoxonium iodide (13.2 g) was added portionwise to a stirred, ice-cooled, suspension of sodium hydride (60% w/w dispersion in mineral oil. 2.4 g; the oil was removed by washing the solid with petroleum ether) in dry dimethylformnamide (80 ml) under an atmosphere of argon whilst maintaining the temperature at 5 to 1 °C. The mixture was allowed to warm to room temperature. Solid 1-(6 chloro-2-methylpyrimidin-4-yl)piperidin-4-one (13.5 g) was added to the stirred mixture whilst maintaining the temperature at 20 to 30° C. using an ice-bath. The mixture was then stirred at room temperature for 16 hours.

The mixture was poured into water (800 ml) and the mixture was extracted with diethyl ether (4×300 ml). The ether extracts were combined, washed with water, dried (Na$_2$SO$_4$) and evaporated. The residue was purified by column chromatography on alumina (ICN alumina N32-63), using 30% dichloromethane in isohexane as eluent to give 6-(6-chloro-2-methylpyrimidin-4-yl)-1-oxa-6-azaspiro[2.5] octane (9.1 g) as a white solid.

$^1$HNMR (CDCl$_3$): 1.5 (m, 2H), 1.9 (m,2H), 2.45 (s, 3H), 2.75 (s, 2H), 3.6 (m, 2H), 4.05 (m, 2), 6.40 (s, 1H); m/z 240 (m+1).

A mixture of 6-(6-chloro-2-methylpyrimidin-4-yl)-1-oxa-6-azaspiro[2.5]octane (7.6 g) and benzyl-1 piperazinecarboxylate (14.0 g) in isopropanol (108 ml)/water (12 ml) was heated to reflux. The resulting solution was stirred at reflux for 3 hours. The solution was evaporated to dryness. The residual oil was dissolved in dichloromethane (300 ml) and the solution was washed with water (3×50 ml) and saturated brine(50 ml), dried (Na$_2$SO$_4$) and evaporated to dryness. The residue was purified by high pressure liquid, column chromatography on silica, using 2% methanol in dichloromethane as eluent, to give 1-benzyloxycarbonyl-4-[1-(6-chloro-2-methylpyrimidin-4-yl)-4-piperidyl-4-olmethyl] piperazine (11.0 g) as a gum.

¹HNMR (CDCl₃): 1.45 (m, 2H), 1.6 (m, 2H), 2.35 (s, 2H), 2.47 (s, 3H), 2.6 (m, 4H), 3.08 (m, 1H), 3.25 (m, 2H), 3.5 (m, 4H), 4.2 (m, 2H), 5.15 (s, 2H), 6.35 (s, 1H), 7.35 (m, 5H); m/z 460 (M+1).

A mixture of 1-benzyloxycarbonyl-4-[1-(6-chloro-2-methylpyrimidin-4-yl)-4-piperidyl-4-olmethyl]piperazine (11.0 g), palladium on charcoal (10% w/w. 0.5 g) and ethanol (100 ml) was agitated under an atmosphere of hydrogen at 25° C. for 2 hours, until hydrogen uptake was complete. The mixture was filtered and the filtrate was evaporated to give 4-[1-(6-chloro-2-methylpyrimidin-4-yl)-4-piperidyl-4-olmethyl]piperazine hydrochloride (7.4 g) as a foam.

NMR (d6-DMSO): 1.45 (m, 4H), 2.3 (s, 2H), 2.47 (s, 3H), 2.7 (m, 4H), 3.0 (m, 4H), 3.25 (m, 4H), 4.0 (m, 2H), 4.35 (s, 1H), 6.6 (d, 1H), 8.0 (d, 1H); m/z 292(M+1).

EXAMPLE 10

Using an analogous procedure to that described in Example 9, 1-(2-methylpyrimidin-4-yl)-4-(1-piperazinemethyl)piperidin-4-ol hydrochloride was reacted with the appropriate sulphonyl chloride to give the compounds listed below in table 4.

TABLE 4

| No. | R | mp ° C. | ¹H NMR (CDCl₃) |
|---|---|---|---|
| 1 | 4-bromo-phenyl | 169–171 | 1.5(m, 4H), 2.35(s, 2H), 2.5(s, 3H), 2.73(m, 5H), 3.03(m, 4H), 3.25(m, 2H), 4.15(m, 2H), 6.30(d, 1H), 7.6(m, 2H), 7.75(m, 2H), 8.10(d, 1H). |
| 2 | phenyl | 94–96 | 1.5(m, 4H), 2.35(s, 2H), 2.48(s, 3H), 2.75(m, 5H), 3.05(m, 4H), .25(m, 2H), 4.15(m, 2H), 6.30(d, 1H), 7.6(m, 3H), 7.77(m, 2H), 8.10(d, 1H). |
| 3 | 4-methoxy-phenyl | 178–180 | 1.45(m, 4H), 2.35(s, 2H), 2.47(s, 3H), 2.73(m, 4H), 2.78(s, 1H), 3.0(m, 4H), 3.25(m, 2H), 3.9(s, 3H), 4.15(m, 2H), 6.30(d, 1H), 7.0(m, 2H), 7.7(m, 2H), 8.10(d, 1H). |
| 4 | 4-methyl-phenyl | 172–174 | 1.47(m, 4H), 2.35(s, 2H), 2.5(m, 6H), 2.72(m, 4H), 2.77(s, 1H), 3.0(m, 4H), 3.23(m, 2H), 4.15(m, 2H), 6.30(d, 1H), 7.35(m, 2H), 7.65(m, 2H), 8.08(d, 1H). |
| 5 | 4-chloro-phenyl | 153–155 | 1.47(m, 4H), 2.35(s, 2H), 2.5(s, 3H), 2.75(m, 5H), 3.03(m, 4H), 3.25(m, 2H), 4.15(m, 2H), 6.30(d, 1H), 7.55(m, 2H), 7.7(m, 2H), 8.10(d, 1H). |

EXAMPLE 11

1-(4-Chlorophenylsulphonyl)-4-[1-(2,6-dimethylpyrimidin-4-yl)-4-piperidylcarbonyl]piperazine (603 mg, 0.96 mol) was refluxed in THF (5 ml), borane-dimethyl sulphide complex was added continuously and reflux continued for 4 hours. Reaction was stirred over a weekend to a residue. THF (5 ml) was added followed by 0.2 μL 6M HCl and stirred for 6 hours. Reaction basified by addition of dilute NaOH and partitioned between DCM and H₂O. Organic layer was sepearted and dried in vacuo affording a white solid. Further purification by filtration column chromatography (silica) DCM to 10% MeOH/DCM and concentration of relevant fractions afforded 1-(4-chlorophenylsulphonyl)-4-[1-(2,6-dimethylpyrimidin-4-yl)-4-piperidylmethyl]piperazine a white solid/foam, 0.39 g (80%), mp73–74° C.;

¹HNMR: 1.1 (m, 2H), 1.75 (m,3H), 2.2 (m, 2H), 2.5 (m, 4H and s, 3H), 2.8 (m, 2H), 3.05 (m, 4H), 4.4 (m,2H), 6.15 (s,1H), 7.7 (m, 4H).

The 1-(4-Chlorophenylsulphonyl)-4-[1-(2,6-dimethyipyrimidin-4-yl)-4-piperidylcarbonyl]piperazine intermediate was isolated, mp 173–174° C.

¹HNMR: 1.75 (m, 4H), 2.3 (s, 3H), 2.5 (s, 3H), 2.7 (m,1H), 2.9 (m,2H), 3.1 (m, 4H), 3.7 (m, 4H), 4.4 (m, 2H), 6.2 (s, 1H), 7.6–7.8 (dd, 4H)

EXAMPLE 12

A solution of 4-bromophenylsulphonyl chloride (370 mg) in methylene chloride (5 ml) was added dropwise over 5 minutes to a mixture of 4-[1-(2-methylpyrimidin-4-yl)-4-piperidylmethyl)-3-oxypiperazine hydrochloride (730 mg) and triethylamine (0.92 ml) in dichloromethane (20 ml) at 0° C. The solution was stirred at ambient temperature for 18 hours. The solution was diluted with dichloromethane and washed with water, dried (Na₂SO₄) and evaporated. The residue was purified by neutral Alumina chromatography eluting with 0–2% methanol in dichloromethane to give as a white solid 1-(4-bromophenylsulphonyl)-4-[1-(2-methylpyrimidin-4-yl)-4-piperidylmethyl]-3-oxypiperazine (359 mg), mp 158–159° C.

¹HNMR (CDCl₃): 1.20 (m, 2H), 1.65 (m, 2H),1.95 (m, 1H), 2.50 (s, 3H), 2.80 (m, 2H), 3.25 (d, 2H), 3.35 (t, 2H), 3.45 (t, 2H), 3.70 (s, 2H), 4.40 (m, 2H), 6.30 (d, 2H), 7.65 (d, 2H), 7.70 (d, 2H), 8.10 (d, 1H); m/z 510 (M+1).

A solution of benzyl chloroformate(15 ml) in methylene chloride (50 ml) was added dropwise to a mixture of ethylisonipecotate (15.7 g) and triethylamine (15 ml) in methylene chloride (250 ml) at 0° C. The solution was stirred to ambient temperature for 2 hours. The solution was washed with water (×2),0.5M Citric Acid, water then Saturated brine, dried (PS paper) and evaporated to give as a colourless oil 1-benzyloxycarbonyl-4-ethoxycarbonyl-piperazine(30 g) which was used directly in the next step without futher purification or characterisation.

To a mixture of oil 1-benzyloxycarbonyl-4-ethoxycarbonyl-piperazine (30 g) in tetrahydrofuran (200 ml) was added lithiumborohydride (2.7 g) and stirred at 60° C. for 5 hours. To quench the mixture, added methanol, dilute hydrochloric acid and then concentrated hydrochloric acid. Diluted with diethylether and resulting suspension washed with water (×2) dilute sodiumbicarbonate then brine, dried (MgSO₄) and evaporated to give as a colourless oil oil 1-benzyloxycarbonyl-4-hydroxy-piperazine (23 g) which was used directly in the next step without further purification or characterisation.

A solution of methanesulphonyl chloride (7.7 ml) in dichloromethane (50 ml) was added dropwise to a stirred ice cooled mixture of oil 1-benzyioxycarbonyl4-hydroxy-piperazine (23 g) and triethylamine (15 ml) in dichloromethane (350 ml). Stirred for 1 hour at 50° C. then washed with water (×4) then brine and dried (PS paper) and evaporated to a colourless oil which set solid, filtered from carbontetrachloride to give 1-benzyloxycarbonyl-4-sulphonyl-piperazine chloride(20 g) as a white solid.

¹HNMR (CDCl₃): 1.25 (m, 2H),175 (m, 2H), 1.94 (m, 1H), 2.78 (m, 2H), 3.0 (s, 3H), 4.06 (d, 2H), 4.23 (m, 2H), 5.15 (s, 2H), 7.4 (m, 5H);m/z 328 (M+1),350 (M+Na).

To a solution of 1-Boc protected-3-oxypiperazine (1.66 g) in dimethylacetamide (15 ml) was added sodium hydride 60% dispersion in mineral oil (146 mg) stirred at ambience for 18 hours in an inert atmosphere. To this mixture was added 1-benzyloxycarbonyl-4-sulphonyl-piperazine chloride (1.81 g) as a solid in one portion and heated to 60° C. for several hours. The mixture was diluted with dichloromethane and washed with water (×3), dried ($Na_2SO_4$) then evaporated to a gum which was chromatographed on silica eluting with 0–3% methanol in dichloromethane to give 1-tert-butyloxycarbonyl-3-oxo-4-[1-(benzyloxycarbonyl)-4-piperidylmethyl]piperazine as an oil (1.36 g)

$^1$HNMR ($CDCl_3$):1.21 (m, 2H), 1.50 (s, 9H), 1.63 (m, 2H), 1.90 (m, 1H), 2.78 (m, 2H), 3.30 (m, 2H), 3.35 (t, 2H), 3.63 (t, 2H), 4.27 (s, 2H), 4.20 (m, 2H), 5.10 (s, 2H), 7.34 (m, 5H);M/z 433 (M+1),449 (M+$NH_3$),376 (m-$C_4H_8$)

To a mixture of 1-tert-butyloxycarbonyl-3-oxo-4-[1-(benzyloxycarbonyl)-4-piperidylmethyl]piperazine (1.35 g), palladium on charcoal (10% w/w, 0.1 g) and ethanol (20 ml) was agitated under an atmosphere of hydrogen at 25° C. for 2 hours until hydrogen uptake was complete. The mixture was filtered and the filtrate was evaporated to give an oil which was mixed with 2,4-dichloro-6-methylpyrimidine (502 mg), ethanol (20 ml) and triethylamine (0.86 ml), heated to reflux for 18 hours. The cooled mixture was evaporated then diluted with dichloromethane and washed with water, dried ($Na_2SO_4$) then filtered onto a silica column (10 g Bond Elut) eluting with 0–5% methanol in dichloromethane to give 1-tert-butyloxycarbonyl-3-oxo-4-[1-(2-methyl-6-chloropyrimidin-4-yl )-4piperidylmethyl] piperazine (1.01 g).

$^1$HNMR ($CDCl_3$): 1.21 (m, 2H), 1.50 (s, 9H), 1.70 (m, 2H), 2.02 (m, 1H), 2.45 (s, 3H), 2.90 (m, 2H) 3.30 (d, 2H), 3.40 (t, 2H), 3.63 (t, 2H), 4.09 (s, 2H), 4.40 (m, 2H), 6.30 (s, 1H); m/z 424 (M+1),
NB 2,4-dichloro-6-methylpyrimidine is available from Aldrich.

To a mixture of 1-tert-butyloxycarbonyl-3-oxo-4-[1-(2-methyl-6-chloropyrimidin-4-yl)-4-piperidylmethyl]piperazine (1.0 g), palladium on charcoal (10% w/w, 0.1 g) and ethanol (20 ml) was agitated under an atmosphere of hydrogen at 25° C. for 18 hours until hydrogen uptake was complete. The mixture was filtered and the filtrate was evaporated to a white solid as 1-tert-butyloxycarbonyl-3-oxo-4-[1-(2-methylpyrimidin-4-yl)-4-piperidylmethyl]piperazine as its monohydrochloride (990 mg).

$^1$HNMR ($CDCl_3$): 1.30 (m, 2H), 1.50 (s, 9H), 1.90 (m, 2H), 2.10 (m, 1H), 2.70 (s, 3H), 3.15 (m, 2H), 3.40 (m, 4H), 3.63 (t, 2H), 4.10 (s, 2H), 4.40 (mn, 2H), 6.60 (d, 390 (M+1),

Ethyl acetate saturated with gaseous HCl (30 ml) was added to 1-tert-butyloxycarbonyl-3oxo-4-[ 1-(2-methylpyrimidin-4-yl)-4-piperidylmethyl]piperazine (980 mg) and the resulting suspension stirred at ambient temperature for 1 hour. The solvent was evaporated to give 4-[1-(2-methylpyrimidin-4-yl)-4-piperidylmethyl]-3-oxypiperazine (1.39 g) as a trihydrochloride. m/z 290 (M+1)

To a solution of diaminoethane (241 g) in ethanol (1200 ml) was added ethylchloroacetate (82.4 g) in ethanol (400 ml) dropwise over 3 hours. The reaction mixture was stirred for a further 90 minutes then added sodium metal (15.6 g) in ethanol (320 ml) precipitate filtered after 20 minutes. The filtrate was evaporated and the residue distilled at 160–170° C. (5 mm Hg) to give a yellow/orange solid which was recrystallised from ethanol to give oxypiperazine (40.4 g).

1-t-butyloxycarbonyl-3-oxypiperazine was prepared as follows. To a solution of oxypiperazine (20 g) in dimethylformamide (400 ml) was added di-t-butyl dicarbonate (48 g). The reaction mixture was stirred at ambient tempature for 30 minutes then evaporated. To the residue was added toluene and the resulting white solid filtered to give 1-t-butyloxycarbonyl-3-oxy piperazine (37.3 g).

EXAMPLE 13

In an analagous method to Example 12 1-(4-trifluoromethylphenylsulphonyl)-4-[1-(2-methylpyrimidin-4-yl)-4-piperidylmethyl]-3-oxypiperazine was prepared as a gum $^1$HNMR:1.20 (m, 2H), 1.65 (m, 2H),1.95 (m, 1H), 2.50 (s, 3H), 2.80 (m, 2H), 3.25 (d, 2H), 3.35 (t, 2H), 3.45 (t, 2H), 3.70 (s, 2H), 4.40 (m, 2H), 6.30 (d, 2H), 7.85 (d, 2H), 7.95 (d,2H), 8.10 (d, 1H).

EXAMPLE 14

A solution of 4-bromobenzoylchloride (0.53 g) in dichloromethane (3 ml) was added to a mixture of 1-(2-methylpyrimidin-4-yl)-4-(piperazin-1-ylcarbonyl) piperidine-4-ol hydrochloride (0.65 g) and triethylamine (1.7 ml) in dichloromethane (30 ml) at 5° C. The solution was stirred at ambient temperature for 18 hours. The resulting solution was evaporated to dryness. The residue was dissolved in dichloromethane and the solution was washed with water, dried ($Na_2SO_4$) and evaporated to dryness. The residue was purified by flash column chromatography on alumina (ICN alumina N32-63), using 0.1–0.4% methanol in dichloromethane as eluent. Recrystallisation from ethyl acetate/isohexane gave 1-(4-bromobenzoyl)-4-[1-(2-methylpyrimidin-4-yl)-4-hydroxy-4-piperidylcarbonyl] piperazine, as a colourless solid (0.53 g), mp114–117° C.

$^1$HNMR (d6-DMSO at 373° K): 1.55 (m, 4H), 2.34 (s, 3H), 2.37 (s, 2H), 2.58 (m, 4H), 3.35 (m, 2H), 3.45 (m, 4H), 3.85 (s, 1H), 3.95 (m, 2H), 6.47 (d, 1H), 7.3 (m, 2H), 7.6 (m, 2H), 8.0 (d, 1H); m/z474 (M+1).

EXAMPLE 15

Using an analogous procedure to that described in Example 14, 1-(2-methylpyrimidin-4-yl)-4-(1-piperazinomethyl)piperidin-4-ol hydrochloride was reacted with 4-fluorobenzoylsulphonyl chloride to give 1-(4-fluorobenzoyl)-4-[1-(2-methylpyrimidin-4-yl]-4-hydroxy-4-piperidylmethyl]piperazine m.p. 114–117° C.

$^1$H-NMR ($CDCl_3$): 1.5 (m, 2H), 1.65 (m, 2H), 2.38 (s, 2H), 2.47 (s, 3H), 2.65 (m, 4H), 3.0 (m, 1H), 3.3 (m, 2H), 3.6 (m, 4H), 4.2 (m, 2H), 6.33 (d, 1H), 7.05 (m, 2H), 7.4 (m, 2H), 8.10 (d, 1H).

EXAMPLE 16

1-(4-Bromophenylsulphonyl)-4-[1-(6-methylpyrimidin-4-yl)-4-piperidylcarbonyl]piperazine (630 mg) suspended in dry THF (10 ml) was treated with excess borane methyl sulphide complex (0.59 ml) at ambient tempature, then at 45° C. for 18 hours. 5M HCl (1.0 ml) was added and stirred for 2 hours. The reaction mixture was basified with 4M NaOH solution. then partitioned between ethylacetate and water. dried (MgSO4), and evaporated. The residue was chromatographed on Bondelut ($CH_2Cl_2$ then 1% MeOH/$CH_2Cl_2$,2% MeOH/$CH_2Cl_2$) to give 1-(4-bromophenylsulphonyl)-4-[1-(6-methylpyrimidin-4-yl)-4-piperidylmethyl]piperazine (276 mg) as a gum.

$^1$H-NMR (CDCl3): 1.05 (m, 2H), 1.6–1.8 (m, 3H), 2.20 (d, 2H), 2.35 (s, 3H) 2.5 (t, 4), 2.80 (t, 2H), 3.05 (t, 4H), 4.35 (m, 2H), 6.35 (s, 1H), 7.6–7.72 (m, 4H), 8.45 (s, 1H); m/z 496 (M+1).

EXAMPLE 17

Using an analogous procedure to that described in Example 16 1-(4-bromophenylsulphonyl)-4-[1-(3-flouro-4-pyridyl)-4-piperidylmethyl]piperazine was prepared.

¹H-NMR (CDCl3): 1.30 (m, 2H), 1.70 (m, 1H), 1.80 (m, 2H), 2.20 (d, 2H), 2.50 (t, 4H), 2.78 (m, 2H), 3.00 (t, 4H), 3.70 (m, 2H), 6.70 (m, 1H), 7.6–7.7 (m, 4H), 8.16 (m, 2H), m/z 499 (M+1).

EXAMPLE 18

The amide 1-(4-bromophenylsulphonyl)-4-[1-(2,6-dimethylpyrimidin-4-yl)-4-piperidylcarbonyl]piperazine (503 mg, 0.96 mmol) was refluxed in THF (5 ml). Borane-dimethylsulphide complex (0.46 ml, 4.8 mmol) was added cautiously and reflux continued for 4 hours. Reaction allowed to stir over weekend allowing reaction to evaporate and hence allowing Me₂S to escape. THF (5 ml) was then added to dry reaction follwed by 0.2 ml 6M HCl and allowed to stir for 6 hours. Reaction was then basified with dilute sodium hydroxide and this was partitioned between DCM and water. Organic layer separated and reduced under vacuum affording a 1-(4-bromophenylsulphonyl)-4-[1-(2,6-dimethylpyrimidine-4-yl)-4-piperidylmethyl]piperazine white foam.

Purification by filtration column chromatography (Silica) DCM→10% MeOH/DCM. Concentration of relevant fractions afforded a white solid/foam, 0.39 g (80%).

m.p.: 73–74° C.

¹HNMR (CDCl₃): 7.7(m, 4H), 6.15(s, 1H), 4.4(m, 2H), 3.05(m, 4H), 2.8(m, 2H), 2.5(m, 4H and s, 3H), 2.2(m, 2H), 1.75(m, 3H), 1.1(m, 2H).

EXAMPLE 19

Borane-dimethylsulphide (0.5 ml; 10M) was added dropwise to a stirred suspension of 1-(4-bromophenylsulphonyl)-4-[1-(4-pyridyl)piperidin-4-ylcarbonyl]piperazine (493 mg) in THF (10 ml) at 0–5°. The mixture was stirred for 18 hours at 25°. 6M Hydrochloric acid (4 ml) was added dropwise and the mixture stirred for 1 hour, then for 0.25 hours at reflux and then for 1 hour at 20°. The mixture was basified to pH 12 with 2M sodium hydroxide. Water (5 ml) was added and the aqueous extracted with dichloromethane (2×25 ml). Combined organic phases were dried and evaporated to give a gum, Trituration with diethyl ether (2×40 ml) gave, as a colourless solid, 1-(4-bromophenylsulphonyl)-4-[1-(4-pyridyl)piperidin-4-ylmethyl]piperazine (257 mg): m.p. 179–180° C:

¹H-NMR(CDCl₃) 1.18(m, 2H), 1.62(m, 1H), 1.74(d, 2H), 2.20(d, 2H), 2.50(t, 4H), 2.78(td, 2H), 3.04(t, 4H), 3.81(d, 2H), 6.62(d, 2H), 7.61(d, 2H), 7.69(d, 2H), 8.22(d, 2H): EI–MS m/z 479 (M+H).

EXAMPLE 20

In a similar manner to Example 19 from 1-(4-bromophenylsulphonyl)-4-[1-(3-chloro-4-pyridyl)piperidin-4-ylcarbonyl]piperazine was prepared 1-(4-bromophenylsulphonyl)-4-[1-(3-chloro-4-pyridyl)piperidin-4-ylmethyl]piperazine: m.p. 158–159° C:

¹H-NMR (CDCl₃): 1.36 (m, 2H), 1.62 (m, 1H), 1.78 (d, 2H), 2.24 (d, 2H), 2.52 (t, 4H), 2.64 (t, 2H), 3.02 (m, 4H), 3.58 (d, 2H), 6.78 (d, 1H), 7.62 (d, 2H), 7.70 (d, 2H), 8.25 (d, 1H), 8.38 (s, 1H): EI–MS m/z 513(M+H).

Formulae

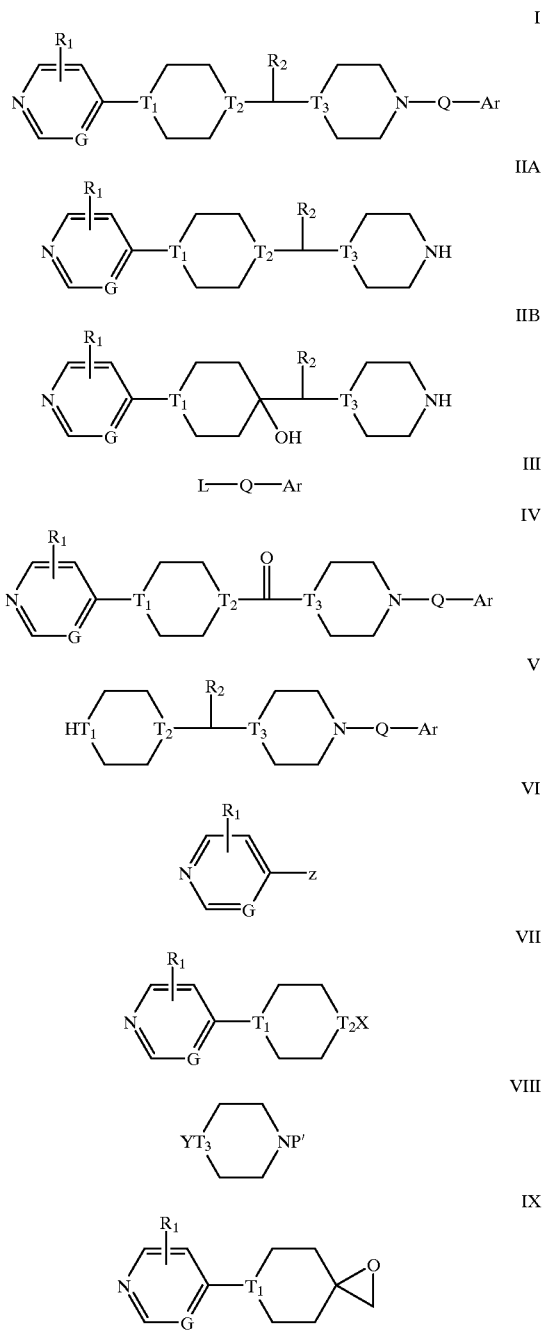

What is claimed is:

1. A compound of formula I, or a pharmaceutically-acceptable salt thereof:

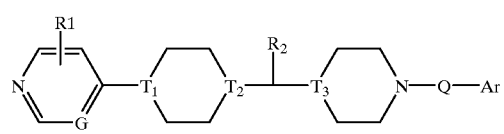

I wherein:
  G is selected from CH or N;
  R1 is selected from hydrogen, halogeno, (1–6C)alkyl, halogeno(1–6C)alkyl, cyano, nitro, (1–6C)alkoxycarbonyl, and $NR^3R^4$ wherein $R^3$ and $R^4$ are independently selected from hydrogen and (1–6C)alkyl, and wherein up to 3 R1 groups may be present;
  $T_1$ is selected from CH or N;
  $T_2$ and $T_3$ are independently selected from N and CR, wherein R is selected from hydrogen, hydroxyl and (C1–4)alkyl and wherein either ring containing $T_2$ or $T_3$ is optionally substituted with an oxo group;
  R2 is selected from hydrogen or (1–6C)alkyl;
  Q is selected from $SO_2$, CO and $CH_2$;
  Ar is selected from a five or six membered heterocycle containing up to 3 heteroatoms selected from nitrogen, oxygen and sulphur, phenyl, phenyl (2–6C)alkenyl and naphthyl in which any Ar group is optionally substituted by one or more substituents selected from (1–6C)alkyl, halogeno, halogeno (1–6C)alkyl, (1–6C)alkoxy, (1–6C)alkoxycarbonyl, cyano, (1–6C)alkylamido, nitro, $NR^3R^4$ wherein $R^3$ and $R^4$ are independently selected from hydrogen and (1–4C)alkyl; provided that both $T_2$ and $T_3$ are not N and that when $T_2$ is CR then $T_1$ is not CH.

2. A compound of formula I as claimed in claim 1 wherein Q is $SO_2$.

3. The compound of formula I as claimed in claim 1 wherein Ar is phenyl.

4. The compound of formula I as claimed in claim 2 wherein Ar is phenyl.

5. The compound of formula I as claimed in any one of claims 1–3 and 4 wherein R1 is hydrogen or (1–6C)alkyl and R2 is hydrogen.

6. The compound of formula I as claimed in any one of claims 1–3 and 4 wherein the rings containing $T_1$ and $T_3$ are unsubstituted.

7. A pharmaceutical composition comprising a compound of formula I as defined in any one of claims 1–3 and 4 and a pharmaceutically acceptable carrier or diluent thereto.

8. A method of treating a disease or medical condition associated with elevated cholesterol levels in warm-blooded animals in need thereof comprising administering to said animal a cholesterol lowering effective amount of a compound of formula I as defined in any one of claims 1–3 and 4.

9. A method of treating a disease or medical condition selected from hypercholesterolemia, atheromatous vascular degeneration and atherosclerosis in a warm-blooded animal in need thereof comprising administering to said animal an effective amount of a compound of formula I as defined in any one of claims 1–3 and 4.

* * * * *